United States Patent

Rheinish et al.

Patent Number: 5,304,182
Date of Patent: Apr. 19, 1994

[54] APPARATUS AND METHOD FOR CURLING AND INSERTING FLEXIBLE INTRAOCULAR LENSES

[75] Inventors: Robert S. Rheinish, Huntington Beach; Allan R. Tonks, Fontana; Thomas P. Richards, Los Angeles, all of Calif.

[73] Assignee: Kabi Pharmacia Ophthalmics, Inc., Monrovia, Calif.

[21] Appl. No.: 950,077

[22] Filed: Sep. 23, 1992

[51] Int. Cl.$^5$ ............................................. A61B 17/00
[52] U.S. Cl. .................................. 606/107; 128/898; 623/6
[58] Field of Search .................. 606/1, 107; 623/4, 6; 128/898

[56] References Cited

U.S. PATENT DOCUMENTS

| | | | |
|---|---|---|---|
| 4,681,102 | 7/1987 | Bartell | 606/107 |
| 4,763,650 | 8/1988 | Hauser | 606/107 |
| 4,765,329 | 8/1988 | Cumming et al. | 606/107 |
| 4,834,094 | 5/1989 | Patton et al. | 606/107 |
| 4,836,201 | 6/1989 | Patton et al. | |
| 4,852,566 | 8/1989 | Callahan et al. | 606/107 |
| 4,862,885 | 9/1989 | Cumming | 606/107 |
| 4,919,130 | 4/1990 | Stoy et al. | 606/107 |
| 4,934,363 | 6/1990 | Smith et al. | 606/107 |
| 5,066,297 | 11/1991 | Cumming | 606/107 |
| 5,098,439 | 3/1992 | Hill et al. | 606/107 |
| 5,100,410 | 3/1992 | Dulebohn | 606/107 |
| 5,190,553 | 3/1993 | Kanert et al. | 606/107 |

OTHER PUBLICATIONS

"Consultation Section" edited by Samuel Masket, M.D., published in J Cataract Refract Surg—vol. 18, Mar. 1992, pp. 206-214.

Primary Examiner—Stephen C. Pellegrino
Assistant Examiner—Glenn Dawson
Attorney, Agent, or Firm—Poms, Smith, Lande & Rose

[57] ABSTRACT

An apparatus and method for folding or curling a flexible lens and for inserting the lens into an eye. The apparatus includes a loading and folding head having a slidable tubular member for curling the lens by constricting a loading chamber within the head, a cannula for entering the eye, and a body housing a plunger for advancing the curled lens out of the loading and folding head and through the cannula. The tubular lens-curling member is configured to enable the lens to curl gently in cooperation with a retaining lip on a wall of the loading chamber, in one smooth, simple and continuous motion.

11 Claims, 2 Drawing Sheets

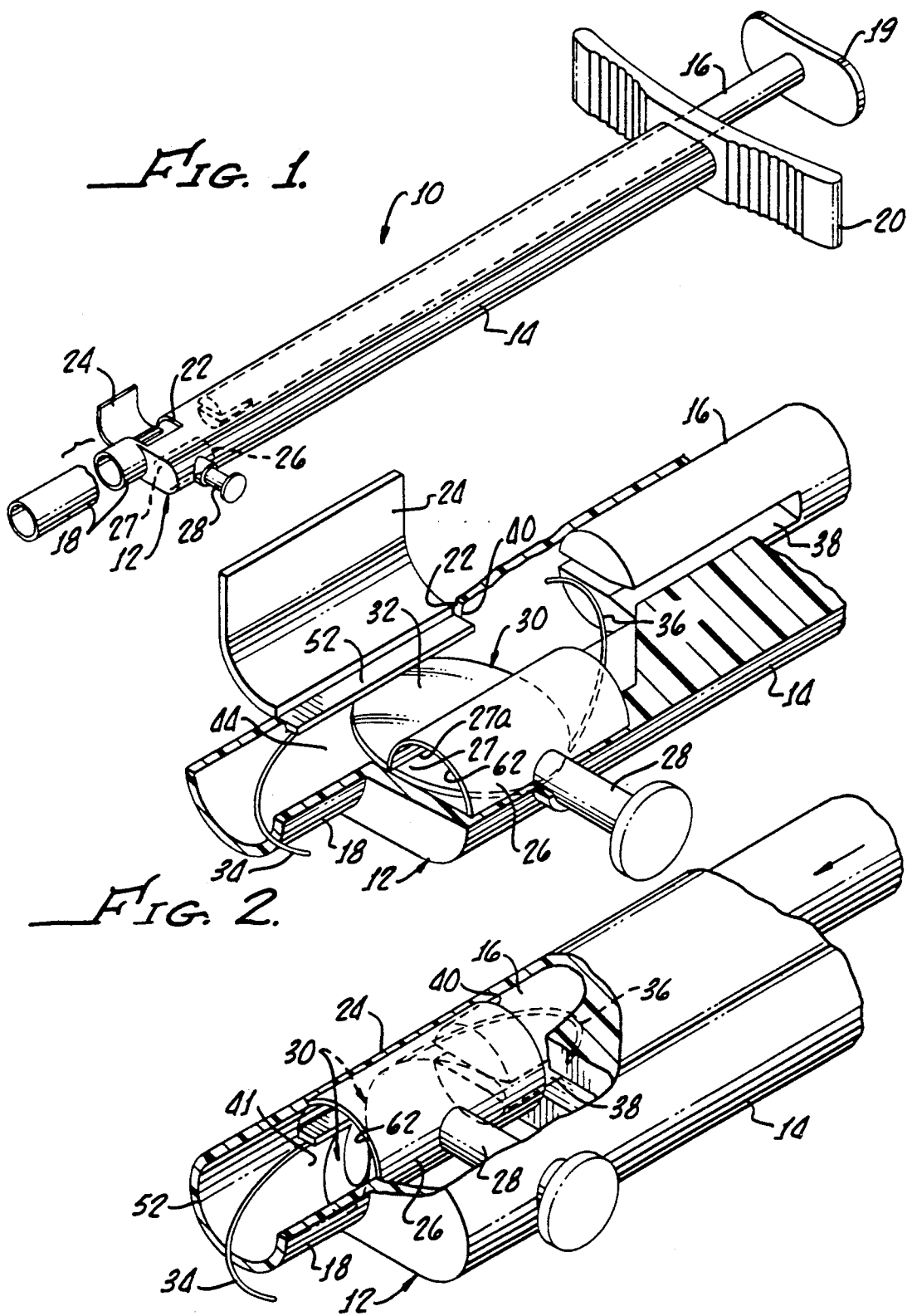

APPARATUS AND METHOD FOR CURLING AND INSERTING FLEXIBLE INTRAOCULAR LENSES

FIELD OF THE INVENTION

The present invention relates to an apparatus and method for implanting of intraocular lenses, and more particularly to an improved surgical instrument and method for inserting a flexible intraocular lens through a small incision.

BACKGROUND OF THE INVENTION

A well known surgical procedure for restoring vision impaired by irreversible malfunctioning of the eye's anatomical lens involves removal of the natural lens and replacement with an artificial intraocular lens, commonly referred to as an IOL.

Early IOL's utilized lenses made of rigid material and having diameters ranging from six millimeters to eight millimeters, necessitating a commensurately large corneal incision for emplacement. More recent developments in IOL technology have made available flexible artificial lenses which are capable of being deformed by bending or curling to achieve a smaller size prior to insertion. This allows the size of the associated corneal incision to be significantly smaller, on the order of three millimeters, thus reducing trauma to the eye, post-operative astigmatism and healing time.

For some years flexible lenses were manipulated by forceps to fold or bend the lenses prior to insertion into the eye. To minimize the risk of scratching of the lenses as well as to reduce the physically exacting difficulty inherent in such manual deformation, a number of lens inserting devices have been proposed. Among these is the device disclosed in U.S. Pat. No. 4,834,094 which involves a sleeve deforming a flexible holder. Other devices are taught by U.S. Pat. No. 4,862,885, wherein the lens is collapsed between two jaws, and U.S. Pat. No. 4,934,363, which claims an external paddle that folds the lens as the paddle is retracted into a rigid tube. While each of these attempted solutions is believed by its inventor to avoid some of the problems of forcep manipulation, unsatisfactory characteristics are clearly present. For example, one such apparatus employs an elaborate and expensive drive mechanism, another involves complex ratchet and pawl operation, and a third requires a membrane along with the lens to be inserted through a cannula into the eye and then the membrane to be withdrawn from the eye.

Modern lenses may be of a three-piece configuration, having a flexible light-focussing central portion called the lens optic, and two extending arm-like members known as haptics, which hold the optic in place after the lens is inserted into the eye.

However, many intraocular lenses still in use today are of one-piece construction, having an integral radial flange fixed to the lens optic, which flange performs the haptic function of centering the optic in place within the eye.

Some previous insertion devices have been designed to manipulate the one-piece configuration of intraocular lens; an apparatus that operates well with both configurations, preparing one-piece and three-piece lenses for insertion with negligible distortion to the lens optic, would be most desirable.

In addition to the risks that may be engendered by prior insertion methods (e.g., scratching of the optic portion of the lens), there is danger of damaging the delicate haptic or fixation members. If a haptic is torn or pinched during lens insertion, the incision may have to be enlarged to permit removal of the damaged lens, thus surrendering the advantages of the smaller incision.

Surgeons who have used existing lens insertion devices have expressed that a highly satisfactory instrument would provide (1) reliable and safe release of the IOL into the eye, (2) minimal wound enlargement, (3) freedom from damage to lens optic and haptic, and (4) ease of loading the IOL into the instrument.

Accordingly, it is an object of this invention to provide a simple and inexpensive method of curling a flexible intraocular lens prior to insertion into an eye so that manual handling of the lens is minimized, reducing the danger of haptic tearing and of lens optic scratching.

Another object is to provide an instrument that will safely accommodate and implant flexible lenses with or without haptic members, i. e., of both one-piece and three-piece construction.

A further object is to provide an easy to load and operate instrument that implants a lens without requiring the insertion into the eye and withdrawal of any membrane-like part of the instrument.

SUMMARY OF THE INVENTION

This invention provides a surgical device and method for easily and reliably deforming a foldable intraocular lens and then inserting it through a smaller incision than would be necessary if the lens were in its original relaxed state.

In accordance with one aspect of the invention, there is provided a loading and folding head on a tubular body, a plunger capable of reciprocating axially within the body, and a cannula projecting from the loading and folding head.

The loading and folding head houses a partially cylindrical lens-curling member of C-shaped cross-section disposed longitudinally of the loading and folding head and having a lens-receiving aperture. The lens-curling member is provided with a means, for example a pushrod projecting externally from the loading and folding head, for laterally displacing by an operator of the lens-curling member within and transversely of the loading and folding head from a first position to a final position.

In its first position, i.e., with the pushrod fully extended externally, the lens-curling member together with the interior of the loading and folding head constitutes a laterally constrictable loading chamber having two opposing vertical walls connected by a planar base, and having unconstricted dimensions suitable to accommodate an intraocular lens in its unfolded state. The loading chamber wall that is opposite the lens-curling member in its first position is provided with a longitudinally disposed retaining lip situated above the planar base to accept a peripheral edge of an intraocular lens beneath the lip.

The intraocular lens is emplaced in the fully extended loading chamber, i.e, with the lens-curling member being in its first position, so that one edge of the lens rests within the lens-receiving aperture while the diametrically opposite edge of the lens is retained by the lens-retaining lip. The lens-curling member is then displaced transversely of the loading and folding head until the lens-receiving aperture engages the lens-retaining lip, placing the lens-curling member in its final position where it forms with the associated loading chamber wall an essentially cylindrical shape, and has thereby curled the lens into a shape and size more suited for insertion through a small incision.

This essentially cylindrical shape forms a base portion of the cannula within the loading and folding head, and is longitudinally in axial alignment with the plunger in the tubular body. The external distal portion of the cannula projects axially from the internal cannular base portion at the distal end of the tubular body and forms an insertion probe.

The axially reciprocal plunger is adapted to engage the curled intraocular lens, advancing it out of the loading chamber through the cannula and into the eye. The plunger may include a slot in its distal tip for protectively accepting a trailing haptic of the intraocular lens during the advancement process.

BRIEF DESCRIPTION OF THE DRAWINGS

FIG. 1 is an isometric view of the lens-folding and insertion device;

FIG. 2 is an enlarged fragmentary view of the loading and folding head, portions being broken away and sectioned;

FIG. 6 is an isometric transparent view of the distal end of the tube body, showing the curled lens and plunger tip as an intraocular lens is ejected into the cannular probe.

DETAILED DESCRIPTION OF THE PREFERRED EMBODIMENT

Figure 3:
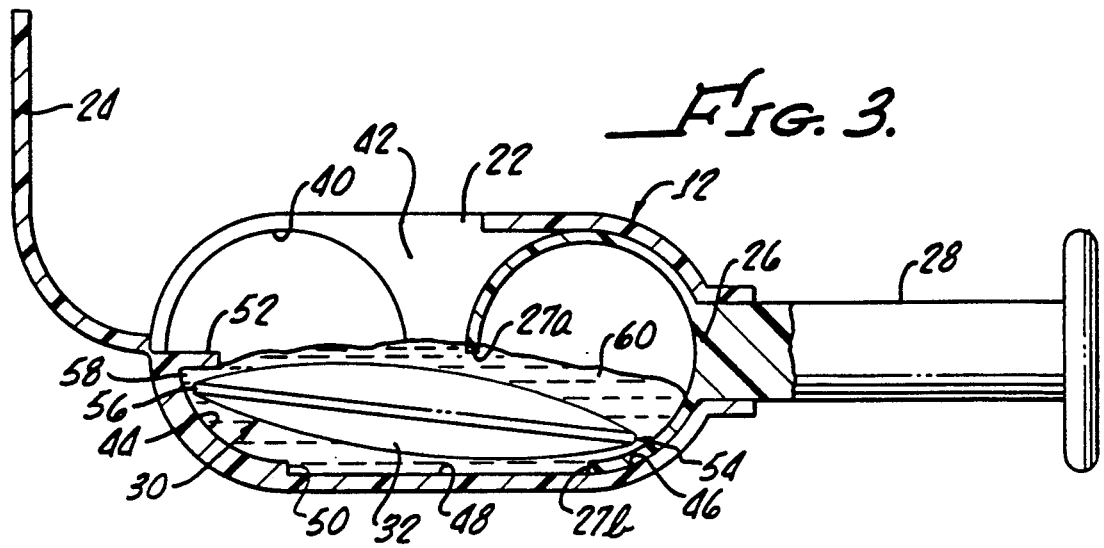
FIGS. 3, 4 and 5 are vertical sectional views showing the loading and folding head in different stages of operation.

Referring to FIG. 1, an instrument 10 constructed in accordance with the present invention includes a loading and folding head 12 at the distal end of a main tubular body 14. Body 14 has a plunger 16 and a cannula 18 (shown partially) extending from head 12. Plunger 16 is advanced axially within the main body 14 by means of a thumb piece 19 and finger pulls 20 until a curled intraocular lens is expelled from the loading and folding head 12 out through the cannula 18, employing the apparatus and process for curling the lens described hereafter.

A lens-admitting opening 22 shown in head 12 provides access for loading of the intraocular lens prior to bending or curling it, and a loading access door 24 provides closure of the opening against contamination, damage or loss after the lens is in place.

A first position of lens-curling member 26 provided with a longitudinal lens-receiving aperture 27 is shown by dotted lines in FIG. 1 and more fully exposed in cutaway FIG. 2 and sectional FIG. 3. Lens-curling member 26 is in the shape of a cylinder having an inner diameter at least as large as the radius of the intraocular lens optic to be curled, and a longitudinal dimension at least as large as the diameter of that lens optic. A circumferential arc of the cylinder wall which subtends a radial angle of approximately 90 degrees is empty, and constitutes lens-receiving aperture 27 defined by aperture edges 27A and 27B in the lower left quadrant of lens-curling member 26 as shown in FIG. 3.

A pushrod 28 is shown to be affixed to lens-curling member 26 and is fully extended out from head 12 when lens-curling member 26 is in its first position. A flexible intraocular lens 30 having optic member 32 and haptic 34 (leading) and 36 (trailing) is placed with no deformation within head 12 so that leading haptic 34 projects into cannula 18 and trailing haptic 36 is positioned for receiving into protective slot 38 in the distal tip of plunger 16. FIG. 2 also illustrates head inlet end 40 (seen more clearly in FIG. 3), through which the tip of plunger 16 advances intraocular lens 30, and head outlet end 41, through which intraocular lens 30 emerges into cannula 18.

Referring to FIG. 3, loading chamber 42 is shown within head 12. First interior wall 44 and second interior wall 46 are separated by planar base surface 48 which joins first wall 44 at a vertically offset line of intersection forming a limiting ridge 50. Lens-curling member 26 is shown in its first position adjacent wall 46, providing maximum transverse operating width to loading chamber 42.

The inner surface of first wall 44 is provided with a longitudinally disposed retaining lip 52 projecting therefrom generally perpendicular to wall surface 44 and generally parallel to planar base surface 48.

Intraocular lens 30 is deposited into loading chamber 42 through opening 22 revealed by the retracting of loading door 24. Leading peripheral edge 54 of lens 30 is placed between edges 27a and 27b of lens-receiving aperture 27, and lens 30 is depressed so that its opposite (trailing) edge 56 is captured beneath retaining lip 52, where lip 52 forms a corner 58 with first wall 44. Lens 30 is thus disposed generally along planar base surface 48 in its pre-deformation state.

A viscoelastic substance 60 may be introduced surrounding lens 30 to provide lubrication and protection of lens 30 during the curling and inserting process to follow. Usage of a viscoelastic material such as Healon®, a registered trademark of Pharmacia of New Jersey, to provide a cushioning of the lens as it is being prepared for expulsion from loading chamber 42. In addition, such material acts as a biocompatible friction-reducing agent facilitating surgical delivery of the folded lens through cannula 18 into the eye.

The presence of retaining lip 52 is an indispensable feature of the apparatus since, in the absence of the lip, the peripheral edge 56 of lens 30, thus unconstrained, would otherwise be free to travel the arcuate surface of first wall 44 when radial pressure is applied at its opposite peripheral edge 54. During the displacement of curling member 26 toward first wall 44, lens 30 would then be subject to significant contact with aperture edge 27a, with damage to the surface of lens optic 32 a clear possibility.

Figure 4:
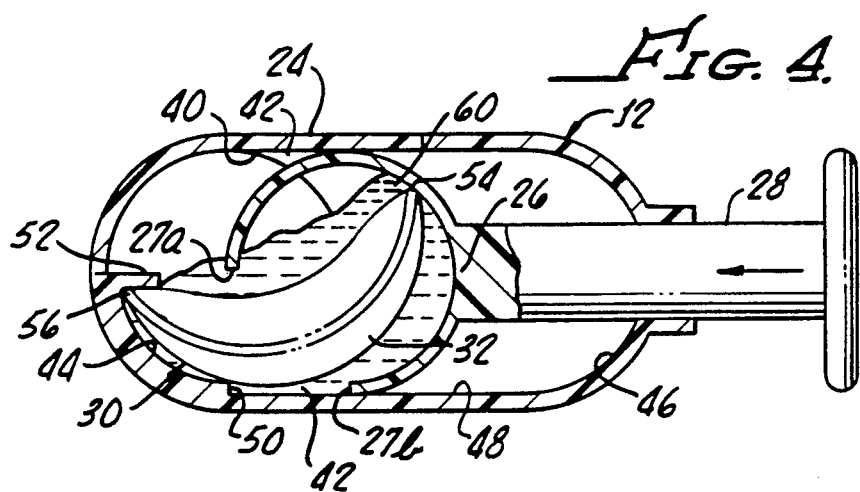

As shown in FIG. 4, loading door 24 is closed after emplacement of lens 30 in loading chamber 42. Lens-curling member 26 is then displaced laterally away from second wall 46 along planar base surface 48 toward first wall 44 by means of pushrod 28. Trailing edge 56 of lens 30 being restrained from upward movement by retaining lip 52, lateral displacement of lens-curling member 26 toward first wall 44 and its retaining lip 52 causes leading edge 54 of lens 30 to follow the arcuate inner surface contour of lens-curling member 26 as the displacement motion exerts centripetal pressure on leading edge 54. Leading edge 54 of lens 30 is thus guided from its rest position adjacent lens-receiving aperture edge 27b toward aperture edge 27a, in constant moving contact with the interior of lens-curling member 26, thereby folding lens 30 generally along that lens diameter parallel to lens-receiving aperture edges 27a, 27b.

Figure 5:
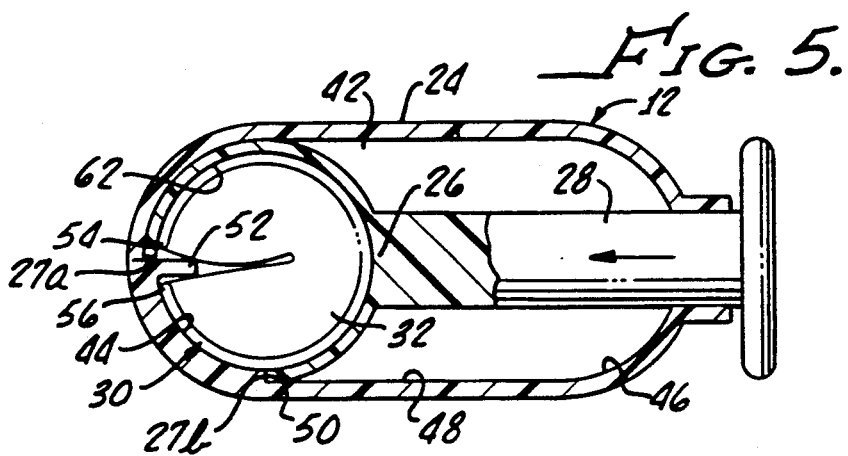

In its final position, lens-curling member 26 having traversed the width of head 12 as shown in FIG. 5, lens-receiving aperture edge 27a engages lens-retaining lip 52, and aperture edge 27b mates with limiting ridge 50, providing a smooth continuous surface formed by the arcuate inner surfaces of first wall 44 and lens-curling member 26. Lens optic member 32 has accordingly been curled to its desirably smallest size and shape with edges 54 and 56 in close mutual proximity, separated effectively only by the minimal depth of retaining lip 52.

The cylinder formed by the inner surface of lens curling member 26 as completed by first wall 44 in the final position of member 26 shown in FIG. 5 constitutes a base portion 62 of cannula 18, as more clearly illustrated in FIG. 6. Inlet 40 of loading and folding head 12 is seen to be the entrance aperture to cannular base 62, and outlet 41 forms the exit aperture thereto. Although the external injection probe portion of cannula 18 is illustrated as having a circular transverse cross section corresponding with circular outlet 41 of cannula base 52, the external probe may also be oval cross section to facilitate the unfolding of lens 30 within the eye. FIG. 6 also shows plunger 16, with distal slot 38 accommodating trailing haptic 36, advancing curled lens 30 through cannular base portion 62 progressively out of outlet 41 toward emergence from cannula 18, with haptic 34 leading the advance.

It is to be understood that the invention is not limited to an embodiment that shows a one-piece construction of these elements. The main body 14, for example, may be made of reusable durable material, while the loading and folding head 12 may be a separate assembly allowing pre-preparation of an intraocular lens before attachment to the main body 14, or permitting disposable detachment therefrom after use, or both. Similarly, the distal external injection probe portion of cannula 18 may be a separate element for ease in sterilization and disposability. Also, the plunger 16 may be manually driven or may be functionally replaced by another such element employing a different source of driving force.

While a preferred form of the invention has been shown in the drawings and described, since variations in the preferred form will be apparent to those skilled in the art, the invention should not be construed as limited to the specific form shown and described, but instead is as set forth in the following claims.

we claim:

1. An apparatus for preparing a flexible intraocular lens for insertion into an eye, said apparatus comprising a lens loading and folding head having an inlet end and an outlet end, said loading and folding head including:
    a loading chamber having first and second opposed walls joined by a generally planar base surface and dimensioned to receive an intraocular lens, each of said walls having an arcuate inner surface and said first wall arcuate inner surface provided with a lens-retaining lip disposed longitudinally above said planar base surface;
    a laterally displaceable, tubular lens-curling member disposed within said loading chamber adjacent to said arcuate inner surface of said second wall, said lens-curling member having an arcuate lens-engaging inner surface with a longitudinal lens-receiving aperture disposed adjacent said planar base surface and dimensioned to engage said lens-retaining lip; and
    means for sliding said lens-curling member laterally along said planar base surface from a first position adjacent said second wall to a second position adjacent said first wall, thus engaging said lens retaining lip.

2. The apparatus of claim 1, wherein said planar base surface is depressed below said first wall arcuate inner surface at the line of intersection of said base surface and said first wall arcuate inner surface to form a limiting ridge, said ridge being dimensioned to effect a smooth continuous mating of said lens-curling member inner surface with said first wall inner surface as said lens-receiving aperture engages said lens-retaining lip.

3. The apparatus of claim 2, wherein said lens-curling member in its second position in engagement with said lens-retaining lip defines together with said arcuate inner surface of said first wall a generally cylindrical lens enclosing space, and said apparatus further comprises a lens injection cannula disposed at said outlet end of said lens loading and folding head, said cannula having a proximal portion formed by said lens enclosing space and a distal injection probe portion external to said loading and folding head, said distal injection probe portion axially aligned with and communicating with said cylindrical lens enclosing space.

4. The apparatus of claim 3 wherein said distal injection probe portion is of oval cross-section.

5. The apparatus of claim 3 wherein said distal injection probe portion is fixed detachably to said loading and folding head.

6. The apparatus of claim 3 further comprising:
    a main body having a tubular bore and a distal end, the lens loading and folding head disposed at said main body distal end, said loading and folding head having an inlet end communicating with said distal end of said main body; and means for axially advancing said folded intraocular lens out of said loading chamber.

7. The apparatus of claim 6 wherein the means for advancing said intraocular lens out of said loading chamber comprises a plunger having a proximal end and a distal end, and longitudinally housed for reciprocal movement axially within said main body.

8. The apparatus of claim 7 wherein said plunger is provided with a slot in its distal end dimensioned to accommodate a trailing haptic of said intraocular lens as said lens is so advanced.

9. The apparatus of claim 6 wherein said main body is removably attached to said loading and folding head.

10. A method of preparing and inserting a foldable intraocular lens into an eye, comprising the steps of:
    providing a loading and folding head having a loading chamber and a displaceable lens-curling member, said loading chamber having a longitudinally disposed lens-retaining lip and said lens-curling member having a lens-receiving aperture dimensioned to engage said lens-retaining lip and having an arcuate inner surface;
    providing a cannula having a distal injection probe portion communicating with said loading and folding head, providing a main body having a tubular bore communicating with said loading and folding head, and providing a plunger longitudinally housed within said main body;
    placing said intraocular lens into said loading and folding head by situating a leading peripheral edge of said intraocular lens into said lens-receiving aperture and locating a diametrically opposite peripheral edge of said intraocular lens beneath said longitudinally lens-retaining lip;
    sliding said lens-curling member laterally within said chamber so that said lens leading peripheral edge is made to follow the contour of said lens-curling member arcuate surface while said opposite peripheral edge of said lens is held relatively fixed by said lens-retaining lip, thus achieving a fully folded lens when said lens-receiving aperture engages said lens-retaining lip; and advancing said plunger to engage said folded lens and eject said lens through said cannula into the eye.

11. The method of claim 10 further comprising the step of introducing viscoelastic material into said loading chamber prior to said lens placing step.

* * * * *